United States Patent [19]

Robson et al.

[11] Patent Number: 5,376,527

[45] Date of Patent: Dec. 27, 1994

[54] PROCESS FOR LYSING MYCOBACTERIA

[75] Inventors: Jillian A. Robson, Pittsboro; Adriann J. Howard; William E. Keating, both of Durham; James A. Down, Cary, all of N.C.

[73] Assignee: Becton Dickinson and Company, Franklin Lakes, N.J.

[21] Appl. No.: 10,467

[22] Filed: Jan. 28, 1993

Related U.S. Application Data

[63] Continuation of Ser. No. 809,806, Dec. 18, 1991, abandoned.

[51] Int. Cl.$^5$ .................. C12Q 1/68; C12P 19/34; C12N 1/06
[52] U.S. Cl. .................................... 435/6; 435/91.2; 435/259
[58] Field of Search ..................... 435/6, 91.2, 259

[56] References Cited

FOREIGN PATENT DOCUMENTS

0428197A3 of 0000 European Pat. Off. .
0288618 11/1988 European Pat. Off. .
0393744 10/1990 European Pat. Off. .

OTHER PUBLICATIONS

A. Brisson-Noel et al., *The Lancet* Nov. 4, p. 1069 (1989).
U. Stritharan et al., *Molecular and Cellular Probes* 5:385 (1991).
Saiki, R. (1988) Science, vol. 239, "Primer Directed Enzymatic Amplification of DNA w/a Thermostable DNA Polymerase". pp. 487–491.
Boddinghaus, B. et al. (Aug. 1990) Journal of Clinical Microbiology, vol. 28(8), pp. 1751–1759.
Cormican et al., "Use of polymerase chain reaction for early identification of Mycobacterium tuberculosis in positive cultures", pp. 601–604, Jul. 1992, London GB, Journal Clinical Pathology vol. 45(7).
Cormican et al., "Rapid identification of cultured Mycobacterium tuberculosis by specific primer directed DNA amplification", abstract, Nov. 1991, Edinburgh Scotland, J. Medical Microbiol, vol. 35(5).

*Primary Examiner*—Margaret Parr
*Assistant Examiner*—Lisa Arthur
*Attorney, Agent, or Firm*—David W. Highet

[57] ABSTRACT

The invention provides a rapid process for lysing Mycobacteria. In one embodiment is provided a process for lysing Mycobacteria which comprises exposing the bacteria to a lysis effective amount of heat. The process of the invention is particularly advantageous since only one step is involved, it is expedient compared to prior methods, and little instrumentation is necessary. By practicing the present invention it is possible to lyse Mycobacteria with minimal effort. In addition, practicing the invention results in liberating cellular components including deoxyribonucleic acid (DNA) from Mycobacteria. Not only is DNA liberated, but the DNA is suited for subsequent analysis by way of probe hybridization, restriction enzyme analysis, and the like.

28 Claims, No Drawings

PROCESS FOR LYSING MYCOBACTERIA

This application is a continuation of application Ser. No. 07/809,806, filed Dec. 18, 1991 now abandoned.

FIELD OF THE INVENTION

The invention is in the field of molecular biology. In particular the invention is in the area of cell lysis. Most particularly the invention is a process for lysis of Mycobacteria.

BACKGROUND OF THE INVENTION

Mycobacteria are a large, diverse, and widely distributed family of aerobic, nonsporulating, nonmotile bacilli that have a high cell-wall lipid content and a slow growth rate. Members of the Mycobacterium genus vary tremendously in virulence. Some Mycobacteria are harmless while others like *M. tuberculosis* are significant pathogens. Mycobacterium species are differentiated by their growth rate, pigment production, animal virulence, and biochemical reactivity.

Many detection methods for determining the presence of pathogenic organisms such as those in the Mycobacteriaceae family rely on the lysis of those organisms. However, commercial and published lysis procedures for Mycobacteriaceae are expensive, laborious, time consuming and may require caustic reagents, specialized equipment, or both. This contrasts with lysis protocols for other types of cells which generally do not require as stringent conditions for lysis.

Recent advances in mycobacterial genetics and increased interest in opportunistic pathogens in patients like those suffering from acquired immunodeficiency syndrome have focused attention to the fact that a procedure for rapid lysis of Mycobacteriaceae is needed. It would be advantageous to have a process for lysing Mycobacteria that is simple, fast, and not disruptive to the material desired from the lysis.

SUMMARY OF THE INVENTION

The present invention provides a process for lysing Mycobacteria that is simple, fast, and not disruptive to the material desired from the lysis. In one embodiment is provided a process for lysing Mycobacteria which consists essentially of exposing the mycobacteria to a lysis effective amount of heat.

Further embodiments include isolating specific cellular components liberated from lysis of Mycobacteria using the process of the invention.

Specific embodiments also include the additional step of isolating nucleic acid from Mycobacteria and amplifying nucleic acid obtained from practicing the process of the present invention.

Other embodiments include the addition of a Mycobacteria identifying agent to the lysed Mycobacteria to identify the presence of Mycobacteria.

The process of the invention is particularly advantageous since only one step is involved, it is expedient compared to prior processes, and little instrumentation is necessary. By practicing the process of the invention it is possible to lyse Mycobacteria with minimal effort. In addition, practicing the invention results in liberating deoxyribonucleic acid (DNA) from Mycobacteria. Not only is DNA liberated, but the DNA liberated is suited for subsequent analysis by way of probe hybridization, restriction enzyme analysis, amplification, and the like.

As used in this document, "lysis effective amount of heat" refers to that amount of elevated temperature which liberates intracellular components such as DNA, RNA, and the like, but which amount does not destroy or render the desired intracellular component unsuitable for subsequent use.

DETAILED DESCRIPTION OF THE INVENTION

The present invention allows for the lysis and resultant liberation of DNA and cellular material from Mycobacteria.

The heating of Mycobacteria for lysis is advantageous over known methods for lysis of Mycobacteria which involve the use of caustic chemicals, time consuming culturing, and mechanical methods which use the French press, the Hughes press, sonicating probes, bath sonicators, freeze-thawing, glass beads, the Ribi pressure cell, and the like (see Table 1). The use of heat can kill pathogenic organisms, thus simultaneous liberation of intracellular components and rendering of safe samples can be obtained by the process of the invention.

Although numerous enzymes and procedures exist for lysing a variety of organisms, the application of heat to lyse Mycobacteria is unique. Mycobacteria are notorious for their inability to readily lyse. Those procedures that do result in lysis of Mycobacteria also generally destroy the contents of the cell that were desired. If the contents of the cell were not destroyed from the lysis procedure, it was generally the result of timely and laborious protocols. Mycobacteria are extremely resistant to physical stress and can be subjected to concentration and digestion procedures that kill ordinary bacteria (compare Tables 1 and 2). Thus, it is unexpected that heating alone, which can lyse less strenuous bacteria, can also lyse the extraordinarily lysis resistant Mycobacteria. It is also unexpected that heating works so well in lysing Mycobacteria because other, more stringent conditions, do not work. However, the practice of the present invention results in Mycobacteria lysis and subsequent yield of useable pieces of DNA that are suitable for use for a variety of purposes such as detection methods and amplification, as well as liberating RNA and other cellular components. The process of the invention can provide DNA and RNA from the lysed microorganisms in single stranded form.

Table I and II set forth a substantial number of protocols for lysing mycobacteria, all of which require more involvement than the present invention.

TABLE I

COMMERCIAL AND PUBLISHED METHODS FOR LYSIS OF MYCOBACTERIA

| Author/Source | Method | Reference |
|---|---|---|
| GenProbe | 15' sonication with lysing buffer and glass beads | Gen-Probe package insert |
| Pierre et al (1991) | 15' @ 95° C. with 0.1 N NaOH, 2M NaCl, 0.5% SDS | J. Clin. Micro. 29 (4):712–717 |
| Hurley et al (1988) | 3' in minibead beater (Biospec Prod. Bartlesville, OK) with distilled phenol and 0.1-mm zirconium beads | Int. J. Systematic Bacteriology 38(2): 143–146 |
| Labidi | Mycobacteria converted to spheroplasts by growth in 1.4% glycine, 60 ug/ml D-cycloserine, 1 mg/mL lithium chloride, 200 ug/ml | Archs. Inst. Pasteur. Tunis. 655(3–4):261–270 |

TABLE I-continued
COMMERCIAL AND PUBLISHED METHODS FOR LYSIS OF MYCOBACTERIA

| Author/Source | Method | Reference |
|---|---|---|
| | lysozyme, 2 mg/mL EDTA; then pelleted by centrifugation and heated 15' @ 65° C. in 1% SDS. | |
| Butcher et al (1988) | 3 hr @ 37° C. with 10 mg/ml subtilisin; then 3 hr @ 37° C. with 50 mg/ml lysozyme; then 12 hr @ 37° C. with 3 mg/ml pronase and 1% SDS. | Gut 29:1222–1228. |
| Wayne and Gross (1968) | 72 hr @ 37° C. with vigorous aeration; then 24 hr @ 37° C. anerobically with 10 uM EDTA, 1 mg/ml pronase; then 90' @ 56° C. with 5% DOC. | J. Bacteriol. 95(4): 1481–1482. |
| Brisson-Noel et al (1989) | Culture: 15' @ 95° C. with 0.1M NaOH, 2M NaCl, 0.5% SDS Blood: 4 hr @ 37° C. with 10 mg/ml lysozyme; then 16 hr @ 55° C. with 5 mg/ml pro K and 0.1% Triton X-100. | Lancet, 11/4:1069–1071. |
| De Wit et al (1990) | 30' @ 70° C. with 10 mM Tris-HCl, pH 8.5, 1 mM EDTA, 150 mM EDTA; then 3 hr @ 37° C. with buffered phenol: 1.5% SDS (1:1 volume) with orbital shaking. | J. Clin. Micro. 28(11):2437–2441. |
| Roberts et al (1987) | 3 washes with 0.85% NaCl; then 15' @ 20° C. with 70% ethanol; then −70° C. | J. Clin. Micro 25(7): 1239–1243. |
| Picken et al (1988) | 16 hr @ 37° C. with 100 mg/0.8 mL lysozyme; then 1 hr @ 37° C. with 1 mg/ml pro K; then 6 hr @ 50° C. with 2% SDS. | Mol. Cell. Probes 2:289–304 |
| Sjobring et al | SDS; then proteins removed by proteinase K; then precipitated with CTAB. | J. Clin. Micro 28(10):220–2204. |
| Whipple et al (1987) | 2 hr @ 37° C. with 8000U/0.5 mL lipase; then 2 hr @ 37° C. with 5 mg/ml lysozyme; then 16 hr @ 50° C. with 2 mg/ml pro K and 1% SDS; then 10 min 0° C. with 0.4 volumes 5M potassium acetate. | J. Clin. Micro. 25(8):1511–1515. |
| Vary et al (1990) | 3 hr @ 37° C. with 10 mg/ml subtilisin; then 3 hr @ 50° C. with 5 mg/ml lysozyme; then 18 hr with 3 mg/ml pronase and 1% SDS; then 6 hr with fresh 3 mg/ml pronase. | J. Clin. Micro 28(5):933–937 |
| Eisenach et al (1986) | 24–72 hr with D-cycloserine; 30' @ 37° C. with 1 mg/ml lysozyme in 15% sucrose, 50 mM Tris-HCl, 50 mM EDTA; then 10' @ 25° C. with 0.1 mg/ml pro K; then 2 hr @ 37° C. with 1% SDS. | Am. Rev. Resp. Dis. 133: 1065–1068 |
| Patel et al (1986) | 15' in light petroleum: chloroform:buffer (3:1:1) with vortexing and mixing; then centrifugation; then 2–4 hrs @ 37° C. with 10 mg/ml nagarase; then 2–4 hr @ 50° C. with 50 mg/ml lysozyme; then 12–36 hr @ 37° C. with 1% SDS and 3 mg/ml pronase added @ 12 hr intervals. | J. Gen Micro. 132:541–5 |
| Pao, et al | 30' @ 37° C. with 2 mg/ml lysozyme in 25% sucrose, 0.1M EDTA, 50 mM Tris-HCl; then 0.1% SDS in 0.1M Tris-HCl, 0.1M NaCl. | Tubercle 69:27–36. |
| Visuvanathan et al (1989) | 1 hr @ 70° C.; then 18 hr @ 37° C. with about 12.5 mg/ml subtilisin; then 5 hr @ 50° C. with about 31 mg/ml lysozyme; then 12 hr with about 2% SDS and 3 mg/ml pronase; then 8 hr with fresh 3 mg/ml pronase. | J. Micro. Methods 10:59–64. |
| Legend: | SDS, sodium dodecyl sulfate; CTAB, cetyl trimethyl ammonium bromide; pro K, proteinase K; Tris-HCl, Tris(hydroxymethyl) aminomethane hydrochloride; EDTA, ethylene diamine tetraacetic acid. | |

TABLE 2
Examples of Published Lysis Protocols for Nonmycobacterial Cells

| Author/Sample | Method | Reference |
|---|---|---|
| deKloet/yeast | 1' @ 32° C. with 20 U/ml lyticase | J. Micro Meth. 2:189–196 |
| Monsen et al/ streptococci (1983) | 5–60' @ 37° C. with 0.1 mg/ml mutanolysin in 5 mM EDTA, 0.5% Triton X-100 | FEMS Micro. letters 16:19–24. |
| Chassy/gram + Gluffrida bacteria (1980) | 60' @ 37° C. with 1.2 mg lysozyme per 1.0 mg bacterial cells | Appl. Env. Microbiol. 39(1):153–158. |
| Gross-/ mammalian Bellard et al | 12 hr @ 37° C. with 50 mg/ml pro K. | Eur. J. Biochem. 36:32–38 |
| Grimberg/blood et al cell (1989) nucleii | 2 hr @ 37° C. with 1 mg/ml pro K in 10 mM Tris-HCL, 10 mM NaCl, 10 mM EDTA | Nucleic Acids Res. 17(20):8390 |
| Moreno/blood et al (1989) | 1 hr @ 50° C. with 200 ug pro K in 0.4M Tris-HCl, 0.1M EDTA, 1% SDS | Nucleic Acids Res. 17(20):8393 |
| Birnboim &/ E. coli Doly (1979) | 30' @ 0° C. with 2 mg/ml lysozyme; then 5' @ 0° C. with 0.2 N NaOH, 1% SDS | Nucleic Acids Res. 7(6):1513–1523 |
| Klein/E. Coli et al (1980) | 15' @ 20° C. with 1 mg/ml lysozyme in 10 mM Tris-HCl. | Plasmid 3:88–91 |

Subsequent use of cellular components liberated from lysis include identification of Mycobacteria and amplification of nucleic acid by means such as polymerase chain reaction, ligase chain reaction, and the like. Identification can take place by means of Mycobacteria identifying agents. Identifying agents refers to those agents suitable for identifying Mycobacteria which include nucleic acid probes including deoxyribonucleic acid and ribonucleic acid, and the like.

The use of probes, for example, for identifying the presence of a particular Mycobacterium can be employed in a one step identification method. For example, once a sample is obtained, heat is applied to the sample, followed by the addition of an identifying agent. If the sample is a sputum sample, the sample is first digested with liquifying agents like N-Acetyl-L-Cysteine (NALC) and sodium hydroxide. The presence of Mycobacteria can then be detected by a variety of means, depending on the marker (e.g., signal to be detected) chosen for use with the identifying agent. The means for identification of the presence of Mycobacteria is usually dictated by the identifying agent employed. For example, nucleic acid probes (e.g., specific for a Mycobacteria species) are typically labeled with $^{125}I$, $^{32}P$, fluorescent dyes, chemiluminescent or colorimetric enzymes and the like. The marker is then detected, which detection is an indication that the particular Mycobacteria is present. Other means for detection include Southern Blot analysis, electrophoretic gel visualization, and the like. The detection can take place with or without prior amplification, depending on the sample and circumstance.

The process of the invention can be employed once the Mycobacteria have been obtained in the form of a sample such as sputum, or an isolated form. Mycobacteria are isolated from a variety of sources including feces, sputum, urine, serum, tissue, other body fluids or obtained from public or private culture collections, and the like. Mycobacteria obtained from the various sources are typically cultured, which is very time consuming, reaching three to six weeks culture time. However, by practicing the method of the invention, the need to culture can be eliminated. If culturing is not desired, the cells are generally first isolated from the source by conventional sample processing methods then usually pelleted by centrifugation and put into a cell suspension. The Mycobacteria in the cell suspension are then subjected to heat.

The ability to use the process of the invention with a clinical sample is particularly advantageous. The organism from which intracellular components are desired is typically subjected to heat in the range of about 60C. to about 100C. The heat range for a particular organism is readily obtainable by titrating heat within this range against release of desired target molecule from the organism. The heat will lyse the organism with subsequent release of intracellular components. The only limitation on the use of heating is that the particular intracellular component of interest not be susceptible to destruction by the heat. Therefore, intracellular components that are not destroyed by the heat employed to release the components may be obtained by using the process of the invention. A variety of means for heating with the process of the invention are available. Heating means include water baths, microwaves, ovens, and the like.

The process of the invention is particularly beneficial for obtaining DNA or RNA from an organism. The process of the invention allows DNA and RNA to be liberated from organisms in single stranded form. Generally, lysis procedures for obtaining DNA and RNA provide the DNA and RNA in double stranded form, which form is then subjected to extra steps to obtain single stranded DNA or RNA for subsequent use. Thus, the process of the invention provides DNA and RNA in a readily useable form for subsequent use, eliminating time consuming steps such as sodium hydroxide or heat denaturation to obtain single stranded nucleic acid. Most detection and amplification procedures require the DNA and RNA be in single stranded form. A variety of amplification methods are available. For example, polymerase chain reaction (PCR), *PCR Technology*, H. A. Erlich, Ed. (Stockton Press, New York, N.Y., 1989), transcription-based amplification system (TAS), *Proc. Natl. Acad. Sci. USA* 86:1173 (1989), ligation amplification reaction (LAR), *Genomics* 4:560 (1989), ligase based amplification system (LAS), *Gene* 89:117 (1990), and Q B replicase, *Infect. Dis.* 162:13 (1990). The goal of any sample preparation is to render the target molecule accessible and improve sensitivity. Such a goal is obtained by taking into account the way samples are prepared, the specific activity of labelled probes, and the selection of a medium or substance in which the sample is prepared.

The heating time required for obtaining intracellular components ranges from about two minutes to about twenty minutes. The amount of heat and time of heat is readily found by sampling a portion of the mycobacteria to be lysed and examining for signs of lysis (e.g., detection of intracellular components), depending on the source from which the intracellular components is to be obtained.

In the most basic embodiment of the invention a sample (clinical sample or cultured sample) containing the intracellular components desired is heated to obtain readily useable components. The organism to be lysed can be in $H_2O$, but also can be in suitable buffers such as Tris-buffered saline (50 mM Tris-HCl, 150 mM NaCl, pH8.0), Phosphate-buffered saline (50 mM sodium phosphate, 150 mM NaCl, pH8.0), Polymerase chain reaction buffer (10 mM Tris-HCl, pH8.8, 50 mM KCl, 1.5 mM $MgCl_2$), React6 (buffer name React6 is registered by Bethesda Research Labs) (50 mM Tris-HCl, pH7.1, 50 mM NaCl, 50 mM KCl, 6 mM $MgCl_2$), Sodium phosphate (pH 5.0 to 12.0), Trizma 9.0 (Sigma:Trishydroxyaminomethylamine), and detergents such as 0.5% Tween 20 and 0.5% Nonidet P-40. Optionally the heated sample can be centrifuged, making available the supernatant and pellet for subsequent use.

Once the sample is heated, subsequent use of the intracellular components can include amplification, detection, and the like. Further steps involving the released intracellular components include subsequent purification of the desired component. For example, typical purification steps for obtaining DNA from a lysed sample include organic extractions such as phenol/chloroform extractions or solid phase adsorption onto silica surfaces such as glass or diatoms.

The process of the invention can be practiced without prior culturing. Unpurified biological samples from sputum, feces, tissue, blood, serum, and the like, can be lysed by practicing the invention and in the same sample could be identified with a Mycobacteria identifying agent. Thus the method comprises a simplified means for detecting Mycobacteria in a clinical, biological, food or environmental sample.

A typical protocol for lysing Mycobacteria with heat comprises centrifugation of a sample of Mycobacteria for a brief amount of time (e.g., about five minutes) and discarding the resultant supernatant. The pellet of Mycobacteria can then be reconstituted in a buffered mixture. If required, any suitable buffer will work. After a brief incubation period with a lysis effective amount of heat, the desired intracellular components can be isolated. Conventional methods for isolating DNA include phenol:chloroform extractions, glass binding with subsequent elution, and the like. Examples of conventional protocols for isolating DNA are found in references such as T. Maniatis et al., *Molecular Cloning: A Laboratory Manual* (*Cold Spring Harbor Lab*) (1982) and Boom et al., *J. Clin. Micro* 28:495 (1990).

Important Mycobacteria that can be lysed by practicing the present invention include *M. avium, M. gordonae, M. tuberculosis, M. kansasii, M. fortuitum, M. chelonae, M. bovis, M. scrofulaceum, M. paratuberculosis, M. marinum, M. simiae, M. szulgai, M. intracellulare, M. xenopi, M. ulcerans, M. leprae, M. lepraemurium, M. smegmatis, M. flavescens, M. terrae, M. nonchromogenicum, M. malmoense, M. asiaticum, M. vaccae, M. gastri, M. triviale, M. haemophilum, M. africanum, M. thermoresistable,* and *M. phlei.* Several of the Mycobacteria are pathogenic. For example, *M. tuberculosis*, which already infects two billion people and infects an additional seven to nine million people each year, is an important Mycobacteria from an epidemiologic and clinical viewpoint In addition, *M. avium, M. bovis, M. intracellularae, M. africanum, M. leprae, M. chelonae, M. paratuberculosis,* and *M. marinum,* are also significant from an epidemiological and clinical viewpoint.

The practice of the present invention provides a rapid and simple lysis procedure for Mycobacteria that provides DNA, RNA and cellular components for subsequent use in a variety of detection procedures.

The following examples illustrate the specific embodiments of the invention described in this document. As would be apparent to skilled artisans, various changes and modifications are possible and are contemplated within the scope of the invention described.

EXAMPLE 1

Purpose:
Initial demonstration of effect of heat alone for *M. tuberculosis* lysis.
Procedure 3 ml pellets of *Mycobacteria tuberculosis* cultures were prepared by culture in 7H10 media in a BACTEC system (Becton Dickinson, Towson, Md.).

The sample was reconstituted in 0.5 ml H₂O then boiled for 15 minutes.

The lysed sample underwent 2 phenol/chloroform extractions then 2 chloroform/isoamyl alcohol extractions. These were followed by ethanol precipitation overnight at −20° C. Sample was reconstituted in 150 $\mu$l H$_2$O. PCR mixes were set up, each using 50 $\mu$l of the lysate product and then cycled. 10 $\mu$l of the PCR product was run on acrylamide gels (10%). 50 $\mu$l of the original sample was also used for slot blot hybridization analysis using GENE SCREEN Plus hybridization transfer membrane (DuPont catalogue no. NEF-976) according to the manufacturer's protocol.
Results:

The ethidium stained gel of the PCR product indicated that heating released sufficient target DNA to allow it to be amplified by PCR and detected on the gel. The autoradiogram of the blot showed that DNA had been liberated from the Mycobacteria and had hybridized to the radioactive probe.

EXAMPLE 2

Procedure
3 ml pellets of BACTEC *Mycobacteria tuberculosis* cultures were prepared in substantial accordance with the teachings of Example 1.

The sample was reconstituted in 0.5 ml H$_2$O then sonicated at 60° C. for 15 minutes.

The lysed sample underwent 2 phenol/chloroform extractions then 2 chloroform/isoamyl alcohol extractions. These were followed by ethanol precipitation overnight at −20° C. Sample was reconstituted in 150 $\mu$l H$_2$O. PCR mixes were set up, each using 50 $\mu$l of the lysate product and then cycled. 10 $\mu$l of the PCR product was run on acrylamide gels (10%). 50 $\mu$l of the original sample was used for slot blot hybridization analysis.
Results:

The ethidium stained gel of the PCR product indicated that sonication did not release sufficient target DNA to allow it to be amplified by PCR and detected on the gel. The autoradiogram of the blot showed that no DNA hybridized to the radioactive probe and therefore sonication treatment alone released no DNA from the *M. tuberculosis.*

EXAMPLE 3

Procedure
3 ml pellets of BACTEC *Mycobacteria tuberculosis* cultures were prepared in substantial accordance with the teachings of Example 1.

The sample was reconstituted in 0.5 ml H$_2$O plus 25 $\mu$l worth of glass beads. The sample was then boiled for 15 minutes with beads.

The lysed sample underwent 2 phenol/chloroform extractions then 2 chloroform/isoamyl alcohol extractions. These were followed by ethanol precipitation overnight at −20° C. Sample was reconstituted in 150 $\mu$l H$_2$O. PCR mixes were set up, each using 50 $\mu$l of the lysate product and then cycled. 10 $\mu$l of the PCR product was run on acrylamide gels (10%). 50 $\mu$l of the original sample was used for slot blot hybridization analysis.
Results:

The ethidium stained gel of the PCR product indicated that heating in the presence of glass beads released sufficient target DNA to allow it to be amplified by PCR and detected on the gel and the level of amplification appeared to be the same as that done in the absence of glass beads. The autoradiogram of the blot showed that no DNA hybridized to the radioactive probe and therefore heat treatment plus glass beads did not release enough DNA to be detected or the DNA remained bound to the beads. Addition of the beads was considered to not be advantageous to the process of DNA release.

EXAMPLE 4

Procedure
3 ml pellets of BACTEC *Mycobacteria tuberculosis* cultures were prepared in substantial accordance with the teachings of Example 1.

The sample was reconstituted in 0.5 ml of H$_2$O plus ~25 $\mu$l worth of glass beads. Sample was sonicated with the beads at 60° C. for 15 minutes.

The lysed sample underwent 2 phenol/chloroform extractions then 2 chloroform/isoamyl alcohol extractions. These were followed by ethanol precipitation overnight at −20° C. Sample was reconstituted in 150 $\mu$l H$_2$O. PCR mixes were set up, each using 50 $\mu$l of the lysate product and then cycled. 10 $\mu$l of PCR product was run on acrylamide gels (10%). 50 $\mu$l of the original sample was used for slot blot hybridization analysis.
Results:

The ethidium stained gel of the PCR product indicated that sonication with glass beads released target DNA which was amplified by PCR and detected on the gel. However, the level of amplified target observed was less than for the previous successful treatments. The autoradiogram of the blot showed that no DNA hybridized to the radioactive probe and therefore sonication plus glass beads did not release enough DNA to be detected or the DNA remained bound to the beads.

EXAMPLE 5

Procedure 3 ml pellets of BACTEC *Mycobacteria tuberculosis* cultures were prepared in substantial accordance with Example 1.

The sample was diluted into 200 µl of H$_2$O then placed in GEN-PROBE lysing tube which was sonicated at 60° C. for 15 minutes then 300 µl additional H$_2$O was added to the tube.

The lysed sample underwent 4 phenol/chloroform extractions then 2 chloroform/isoamyl alcohol extractions. These were followed by ethanol precipitation overnight at −20° C. Samples were reconstituted in 150 µl H$_2$O. PCR mixes were set up, each using 50 µl of the lysate product and then cycled. 10 µl of the PCR product was run on acrylamide gels (10%). 50 µl of the original sample was used for slot blot hybridization analysis.

Results:

The ethidium stained gel of the PCR product indicated that the Gen-Probe lysis method did release sufficient target DNA to allow it to be amplified by PCR and detected on the gel and the level of amplification appeared to be similar to be levels observed for boiling or boiling with beads. The autoradiogram of the blot showed that DNA hybridized to the radioactive probe indicating that enough DNA was released to be detected. While Gen-Probe was successful, two extra phenol/chloroform extractions were required to clear the sample (i.e. remove contaminants from the lysis solution) before it was subjected to analysis.

EXAMPLE 6

Procedure:

10 µl of 10$^6$/ml BACTEC-cultured *Mycobacteria tuberculosis* was placed in 1 ml of sterile H$_2$O and from this solution 10 µl aliquots were placed in 0.6 ml tubes (=100 organisms/experiment). Each tube received 100 µl of 1×PCR buffer and was incubated for 0, 1, 5, 10, and 15 minutes at 100° C. Following heating, the mixtures containing *Mycobacteria tuberculosis* were centrifuged for 5 minutes in a microcentrifuge (12,000×g) and the pellets and supernatants were subjected to PCR amplification using primers specific for the IS6110 *Mycobacteria tuberculosis* insertion element according to the following thermocycling protocol for 30 cycles: 94° C. 3 min denature, 94° C. 1 min denature, 62° C. 1 min anneal, 72° C. 1 min extension, 72° C. 7 min extension, and 4° C. soak. The amplified products were analyzed on ethidium-stained polyacrylamide gels.

Results:

It was found that all of the heating times produced lysis as shown by production of amplified target; including the 0 time (i.e., no boiling) control. Though initially surprising, this is consistent because the first temperature cycling of the PCR reaction consisted of heating to 94° C. for 3 minutes which appeared to suffice for *Mycobacteria tuberculosis* lysis as evidenced by amplified target. With increased period of heating from 1 to 15 minutes there was a reduction in the signal of amplified target in the pellets, which is consistent with the idea that the heat produced lysis of the organisms and therefore they were not pelleted by centrifugation.

It was concluded that the 94° C. heating produced during the thermocycling reaction was adequate to release amplifiable target DNA from the *Mycobacteria tuberculosis* and that increased incubation with 100° C. prior to the reaction produced increased lysis of *Mycobacteria tuberculosis*.

EXAMPLE 7

Procedure:

Further evidence suggested that 94° C. heating produced during the thermocycling reaction was adequate to release amplifiable target DNA from *Mycobacteria tuberculosis*. One hundred *Mycobacteria tuberculosis* organisms were put directly into a PCR mixture and subjected PCR cycling as described above. A positive control, consisting of 100 copies of plasmid SK4.3 which contains the IS6110 sequence was run concurrently with a negative control which consisted of H$_2$O.

Results:

The amplified targets were analyzed on an ethidium-stained polyacrylamide gel. The positive control containing the IS6110 sequence showed an amplified target while the intact organisms also showed an amplified target but which was about 10 fold stronger in intensity than the positive control which was consistent with the published observation that each *Mycobacteria tuberculosis* organism contains about 10 copies of the IS6110 target sequence.

This experiment corroborated the previous conclusion that the 94° C. heating produced during the thermocycling reaction was adequate to release amplifiable target DNA from the *Mycobacteria tuberculosis*.

Although the invention has been described with respect to specific modifications, the details thereof are not to be construed as limitations, for it will be apparent that various equivalents, changes and modifications may be resorted to without departing from the spirit and scope thereof, and it is understood that such equivalent embodiments are to be included therein.

EXAMPLE 8

Purpose

Identify compatible buffers that, when mycobacteria are boiled in their presence, will:
A. Lyse and release their DNA.
B. Allow this DNA to be amplified.

MATERIALS

BACTEC *M. tuberculosis* Culture Bottle (~10$^6$ orgs/ml)
BACTEC *M. Fortuitum* Culture (~10$^8$ orgs/ml)
NaCl (Fisher #5271-500 Lot #896394)
Na Phosphate (Fisher #5381 Lot #742308)
Na$_3$ Phosphate (Fisher #5377 Lot #78758)
10×TBS pH 8.1 (+2% Azide)
Acetone (Fisher A18-000 Lot #902245)
10% SDS soulution (BRL #5553JA Lot #ARU602)
NP-40 (Sigma #N-6507 Lot #36F-0198)
Tween 20 (BioRad Cat #170-0531 Control #M1419)
Achromopeptidase (Sigma #A-7550 Lot #127F - 68391)
Trizma 9.0 (100 mM Tris 9.0+10 mM NaCl)
10×PCR Buffer (100 mM Tris pH 8.8 500 mM KCl 15 mM MgCl$_2$)

10×REACT 6 (1×50 mM NaCl, Tris, KCI+6 mM MgCl$_2$)

PROCEDURE

Fourteen 1.5 ml screw capped tubes were lined up. To each one, a 2 ml pellet of *M. tuberculosis* was collected. This was also performed with a culture of *M. Fortuitum*.

The following 14 buffers were prepared: (in sterile H$_2$O)

1. Sterile H$_2$O
2. 100 mM NaCl
3. 1×TBS (50 mM Tris-HCl, 150 mM NaCl pH 8)
4. 1×PBS (50 mM Na$_2$Phosphate, 150 mM NaCl pH 8)
5. 1×PCR Buffer
6. 1×React 6 (50 mM Tris-HCl pH21, NaCl, KCI+6 mM MgCl$_2$)
7. Trizma 9.0
8. Trizma 9.0+Achromopeptidase
9. 10% Acetone
10. 0.5% Tween 20
11. 0.5% NP-40
12. 0.5% SDS
13. Sodium Phosphate (50 mM pH 12)
14. Sodium Phosphate (50 mM pH 5)

300 μl of a buffer was added to its appropriate mycobacteria pellet (1 Tb., 1 Fortuitum each) and incubated at 100° C. after vortexing for 30 minutes, except #8. #8 received 300 μl trizma 9.0 plus 36 μl of a 5 mg/ml solution of Achromopeptidase (50 units). This was incubated at 50° C. for 30 minutes, then at 100° C. for 30 minutes.

All samples were phenol/chloroform extracted, then chloroform extracted, and then ethanol precipitated overnight.

Samples were reconstituted into 30 μl of sterile water, then 15 μl of sample plus 5 μl of Type II tracking dye was electrophoressed on 1% Agarose gel in 1×TAE and visualized after ethidium bromide staining.

5 μl of each sample (Tb only) was placed into PCR mixes, containing 0.25 μM of M.Tb. 21 and 22 primers, as well as 2.5 units amplitaq polymerase. Samples were cycled as follows:

| | | | |
|---|---|---|---|
| 94° C. | 3 minutes | Denature | |
| 94° C. | 1 minute | Denature | |
| 62° C. | 1 minute | Anneal | } 30 cycles |
| 72° C. | 7 minutes | Extension | |
| 4° C. | — | Soak | |

10% of each PCR product was electrophoressed on 10% acrylamide gels and ethidium bromide stained.

RESULTS

The agarose gel results indicate that the *M. Fortuitum* samples, which have 100 times more organisms, release more (quantity wise, not percentage wise) DNA than *Mycobacteria tuberculosis*. For *Mycobacteria tuberculosis*, DNA is seen in achromopeptidase/boiled the Tween 20/boiled sample, and 0.5% SDS.

The PCR results show that all 14 buffers cause (*Mycobacteria tuberculosis*) DNA to be released upon boiling, except SDS which is known for inhibiting PCR.

CONCLUSIONS

This data shows that 13 of the 14 buffers tested will liberate *Mycobacteria tuberculosis* DNA when boiled in such amounts that PCR can detect it. The agarose gel shows that the buffers liberate small-sized DNA from *M. Fortuitum*, but not enough organisms were present of *M. tuberculosis*. to allow much DNA to be seen on the gel.

EXAMPLE 9

PURPOSE

To see if we could lyse mycobacteria by boiling them in water.

MATERIALS

| BACTEC cultures of Mycobacteria: | |
|---|---|
| *M. Avium* | 9 × 10$^7$ orgs/ml |
| *M. Scrofulaceum* | 8 × 10$^7$ orgs/ml |
| *M. Intracellularae* | 4 × 10$^8$ orgs/ml |
| *M. Gordonae* | 1 × 10$^7$ orgs/ml |
| *M. Tuberculosis* | 8 × 10$^6$ orgs/ml |
| *M. Kansasii* | 2 × 10$^8$ orgs/ml |
| *M. Fortuitum* | 2 × 10$^8$ orgs/ml |
| *M. Chelonae* | 7 × 10$^8$ orgs/ml |
| *M. Bovis* | 5 × 10$^7$ orgs/ml |

PROCEDURE 1 ml of each species of BACTEC Mycobacteria was harvested and pelleted. Each sample was in 1.5 ml screw-capped tube with conical bottom, and was reconstituted with 100 μl sterile H$_2$O.

All samples were mixed and incubated at 100° C. for 30 minutes. All samples were phenol/chloroform examined twice then ethanol precipitated. Samples were reconstituted in 25 μl of H$_2$O plus 5 μl dye. 15 μl of that was run on 1% agarose gel in 1×TAE.

Gel was stained and visualized under UV light.

RESULTS

The data indicates that DNA is seen in lanes which correspond to the *M. Kansasii* and *M. Fortuitum*, which were the cultures containing the largest numbers of organisms. Inability to observe DNA from the other species probably relates to the lower numbers of organisms in those cultures.

CONCLUSIONS

The data demonstrates that boiling mycobacteria will liberate DNA.

What is claimed is:

1. A process for lysis of Mycobacteriaceae comprising exposing Mycobacterium to a lysis effective amount of heat in the absence of other lysogenic agents and in the absence of other lysogenic conditions.

2. The process of claim 1 in which the Mycobacterium is selected from the group consisting of *Mycobacterium avium*, *Mycobacterium intracellulare*, *Mycobacterium gordonae*, *Mycobacterium tuberculosis*, *Mycobacterium kansasii*, *Mycobacterium fortuitum*, *Mycobacterium chelonae*, *Mycobacterium bovis*, *Mycobacterium scrofulaceum*, *Mycobacterium paratuberculosis*, *Mycobacterium phlei*, *Mycobacterium marinum*, *Mycobacterium simiae*, *Mycobacterium szulgai*, *Mycobacterium leprae*, *Mycobacterium xenopi*, *Mycobacterium ulcerans*, *Mycobacterium lepraemurium*, *Mycobacterium flavescens*, *Mycobacterium terrae*, *Mycobacterium nonchromogenicum*, *Mycobacterium malmoense*, *Mycobacterium asiaticum*, *Mycobacterium vaccae*, *Mycobacterium gastri*, *Mycobacterium triviale*, *Mycobacterium haemophilum*, *Mycobacterium africanum*, *Mycobacterium thermoresistable*, and *Mycobacterium smegmatis*.

3. The process of claim 2 in which the Mycobacterium is *M. tuberculosis*.

4. The process of claim 2 in which the Mycobacterium is *M. bovis*.

5. The process of claim 2 in which the Mycobacterium is *M. africanum*.

6. The process of claim 2 in which the Mycobacterium is *M. intracellularae*.

7. The process of claim 2 in which the Mycobacterium is *M. avium*.

8. The process of claim 2 in which the Mycobacterium is *M. leprae*.

9. The process of claim 2 in which the Mycobacterium is *M. chelonae*.

10. The process of claim 2 in which the Mycobacterium is *M. paratuberculosis*.

11. The process of claim 1 which further comprises isolation of cellular components.

12. The process of claim 11 in which the cellular component isolated is DNA.

13. The process of claim 11 in which the cellular component isolated is RNA.

14. The process of claim 1 which further comprises amplification of mycobacteria nucleic acid.

15. The process of claim 14 in which the nucleic acid is DNA.

16. The process of claim 14 in which the nucleic acid is RNA.

17. The process of claim 3 which further comprises the isolation of DNA.

18. The process of claim 4 which further comprises the isolation of DNA.

19. The process of claim 5 which further comprises the isolation of DNA.

20. The process of claim 6 which further comprises the isolation of DNA.

21. The process of claim 7 which further comprises the isolation of DNA.

22. The process of claim 1 which further comprises the addition of a Mycobacterium identifying agent.

23. The process of claim 22 in which the Mycobacterium identifying agent is a nucleic acid probe.

24. The process of claim 23 in which the nucleic acid probe is deoxyribonucleic acid.

25. The process of claim 23 in which the nucleic acid probe is ribonucleic acid.

26. The process of claim 22 further comprising obtaining the Mycobacterium from a source selected from the group consisting of feces, sputum, blood, tissue, urine, and other body fluids.

27. The process of claim 1 wherein said lysis effective amount of heat does not hydrolyze Mycobacterium nucleic acid.

28. The process of claim 1 wherein said process further comprises a release of a sufficient quantity of Mycobacterium nucleic acid for amplification.

* * * * *